(12) United States Patent
Biber (10) Patent No.: US 9,360,541 B2
(45) Date of Patent: Jun. 7, 2016

(54) LOCAL SHIM COIL WITHIN A LOCAL COIL FOR LOCAL $B_0$ HOMOGENIZATION IN AN MRT EXAMINATION

(75) Inventor: Stephan Biber, Erlangen/Frauenaurach (DE)

(73) Assignee: Siemens Aktiengesellschaft, München (DE)

( * ) Notice: Subject to any disclaimer, the term of this patent is extended or adjusted under 35 U.S.C. 154(b) by 55 days.

(21) Appl. No.: 13/525,198

(22) Filed: Jun. 15, 2012

(65) Prior Publication Data

US 2012/0323113 A1 Dec. 20, 2012

(30) Foreign Application Priority Data

Jun. 17, 2011 (DE) .......................... 10 2011 077 724

(51) Int. Cl.
*A61B 5/055* (2006.01)
*G01R 33/3875* (2006.01)
*G01R 33/34* (2006.01)

(52) U.S. Cl.
CPC ...... *G01R 33/3875* (2013.01); *G01R 33/34046* (2013.01)

(58) Field of Classification Search
USPC .......................................................... 600/422
See application file for complete search history.

(56) References Cited

U.S. PATENT DOCUMENTS

| | | | |
|---|---|---|---|
| 5,111,146 A | 5/1992 | Kuhn | |
| 5,136,244 A * | 8/1992 | Jones et al. | 324/318 |
| 5,650,724 A | 7/1997 | Yamagata | |
| 6,023,167 A | 2/2000 | DeMeester et al. | |
| 6,100,695 A | 8/2000 | DeMeester et al. | |
| 6,157,193 A * | 12/2000 | Renz et al. | 324/318 |
| 6,943,551 B2 | 9/2005 | Eberler et al. | |
| 7,414,401 B1 | 8/2008 | Lvovsky | |
| 7,458,934 B2 * | 12/2008 | Roberts et al. | 600/249 |
| 8,441,258 B2 * | 5/2013 | Chan et al. | 324/318 |
| 2010/0262024 A1 * | 10/2010 | Hu et al. | 600/504 |

FOREIGN PATENT DOCUMENTS

| | | |
|---|---|---|
| DE | 3917619 A1 | 12/1990 |
| DE | 103 14 215 B4 | 11/2006 |

OTHER PUBLICATIONS

German Office Action dated Mar. 22, 2012 for corresponding German Patent Application No. DE 10 2011 077 724.5 with English translation.
C. Juchem et al., "Magnetic Field Homogenization of the Human Prefrontal Cortex with a Set of Localized Electrical Coils," Magnetic Resonance in Medicine 63, pp. 171-180, 2010.
J. Hsu et al., "Mitigation of Susceptibility-Induced Signal Loss in Neuroimaging Using Localized Shim Coils," Magnetic Resonance in Medicine 58, pp. 243-248, 2005.

(Continued)

*Primary Examiner* — Long V Le
*Assistant Examiner* — Kevin Pontius
(74) *Attorney, Agent, or Firm* — Lempia Summerfield Katz LLC (57) ABSTRACT

A local coil for an imaging system, in particular an MRI scanner, is provided. The local coil is an MRI scanner local coil within which the head of a patient may be positioned, and that includes at least one shim coil. A conductor of a shim coil of the at least one shim coil is disposed in a region for a molded nape section of the patient.

25 Claims, 7 Drawing Sheets

(56) References Cited

OTHER PUBLICATIONS

J. L. Wilson et al., "Utilization of an Intra-Oral Diamagnetic Passive Shim in Functional MRI of the Inferior Frontal Cortex," Magnetic Resonance in Medicine 50, pp. 1089-1094, 2003.

R. Cusack et al., "An Evaluation of the Use of Passive Shimming to Improve Frontal Sensitivity in fMRI," NeuroImage 24, pp. 82-91, 2005.

SATPAD, MRI High Resolution Imaging, May 5, 2011, http://www.satpadinc.com.

* cited by examiner

LOCAL SHIM COIL WITHIN A LOCAL COIL FOR LOCAL $B_0$ HOMOGENIZATION IN AN MRT EXAMINATION

This application claims the benefit of DE 10 2011 077 724.5, filed on Jun. 17, 2011.

BACKGROUND

The present embodiments relate to a local shim coil within a local coil for an imaging system.

Magnetic resonance imaging scanners (MRI scanners) for examining patients using magnetic resonance imaging are known, for example, as disclosed by DE10314215B4, U.S. Pat. No. 6,100,695, U.S. Pat. No. 6,023,167.

In MR imaging, images with a high signal-to-noise ratio (SNR) may be recorded using local coils. Local coils are antenna systems that may be provided in the immediate vicinity above (anterior) or below (posterior) a patient. During an MR measurement, excited cores induce a voltage in the individual antennae of the local coils. The voltage may be amplified by a low-noise amplifier (e.g., LNA, preamp) and forwarded in a wired manner to an electronic receiving device. High-field units (e.g., 1.5 T to 12 T and more) may be used to improve the signal-to-noise ratio even in the case of high resolution images.

The homogeneity of the $B_0$ basic field is important in many clinical MR applications. Artifacts or distortions may occur. Some applications, such as FatSat, may no longer operate optimally in the case of differences in the homogeneity. FatSat is a method in which the frequency shift of the protons bound in the fat is used to fade out the signals of fatty tissue by a strong transmission pulse (e.g., a saturation pulse) in the case of the fat frequency. Alternatively, FatSat may use the frequency or the phase shift of the two signals to fade out the fatty tissue, in part, in image processing. Since the difference between the proton frequency in water and in fat is very slight (e.g., a few ppm of the basic field), the FatSat method is highly dependent on the spatial homogeneity of the basic field. The spatial homogeneity is currently determined by way of volumes of approximately 30×30×30 cm (+−20 cm) with up to, for example, approximately 0.5 ppm.

Distortions of the $B_0$ basic field may occur in bodily regions due to the spatially inhomogeneous distribution of the susceptibility ($mu\_r$ or $m_r$) of the body tissue. These distortions may be corrected by shim coils fitted in the MRI scanner system. Current shim coils are installed in the system spatially in the region of the gradient coils, relatively far away from the patient. The number of different shim coils, the arrangement and activation of which allows a certain number of degrees of freedom, may be used to compensate for $B_0$ inhomogeneities of the usually super-conducting basic field magnets using shim currents in conventional copper coils. The number of degrees of freedom is insufficient in many systems to compensate for inhomogeneities in the region of, for example, the cervical spine (HWS). Shim coils of a higher order (e.g., a strong local field variation), which are provided in the system, may be extremely inefficient with respect to current or output versus change in B0.

Shim coils are also described in the following documents: Christoph Juchem et al., *Magnetic field homogenization of the human prefrontal cortex with a set of localized electrical coils*, Journal of Magnetic Resonance Imaging, MRM, 63: 171-180, 2010; GH Glover et al., *Mitigation of susceptibility induced signal loss in neuroimaging using localized shim coils*, MRM 2005, 243-248; R. Cusack et al., *An evaluation of the use of passive shimming to improve frontal sensitivity in fMRI*, Neuroimage, 2005, 24, 82-91; and J L Wilson et al., *Utilization of an intra-oral diamagnetic passive shim in functional MRI scanner of the inferior frontal cortex*, MRM 2003, 50, 1089-1094

According to one current solution (e.g. www.satpadinc.com/photos), gel cushions may be placed in the nape region of the neck of the patient to be examined if the shim orders are not sufficient. The residual susceptibility of such cushions, in the best case scenario, counteracts the B.sub.0 distortions such that a more homogeneous field results.

SUMMARY AND DESCRIPTION

The present embodiments may obviate one or more of the drawbacks or limitations in the related art. For example, the field homogeneity for an imaging system may be optimized. In one example, a local coil for an imaging system (e.g., an MRI scanner) is configured to receive the head of a patient positioned therein and includes at least one shim coil.

In another example, the MRI scanner local coil is configured to shim the magnetic field.

DETAILED DESCRIPTION OF THE DISCLOSURE

Figure 7:
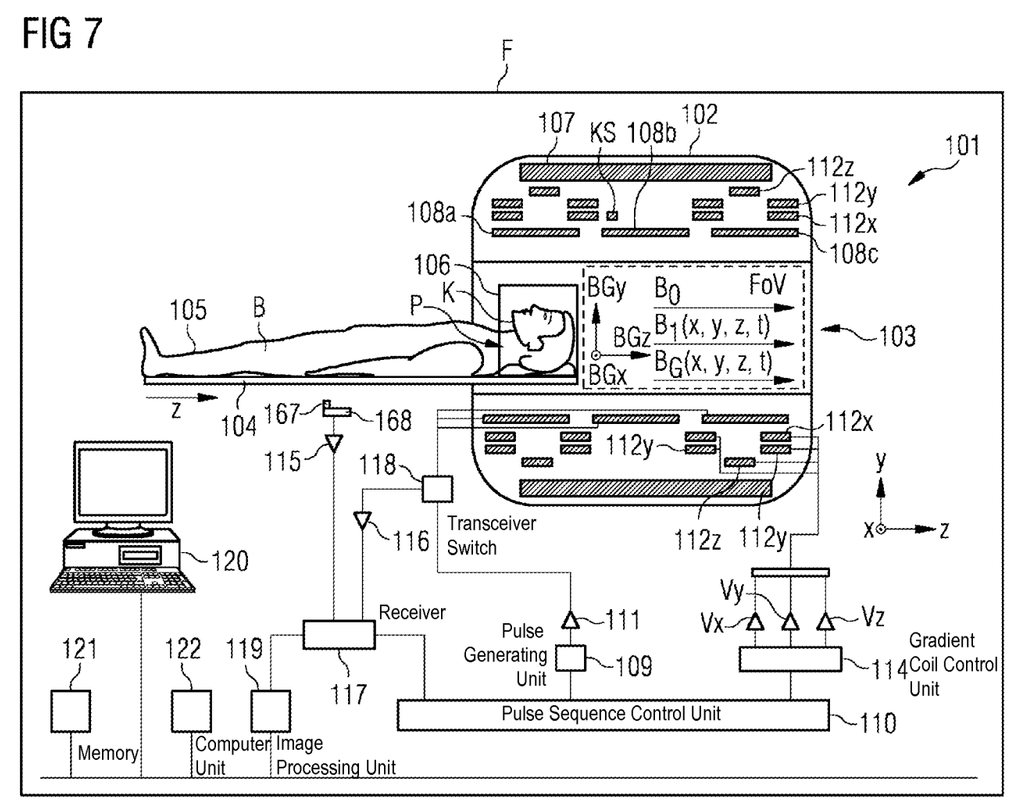
FIG. 7 shows a schematic of an MRI scanner system.

FIG. 7 shows, as background, an imaging scanner MRI scanner 101 located in a screened space or Faraday cage F. The imaging scanner has a whole body coil 102 with, for example, a tubular space 103, in which an examination table 104 with a body of an object to be examined 105 (e.g., a patient; with or without a local coil arrangement 106) may be moved in the direction of the arrow z to generate images of the patient 105 using an imaging method. According to one embodiment, the local coil arrangement 106 may be arranged on the patient in a local region (e.g., a field of view (FOV)) of the MRI scanner. Images of a section of the body 105 may be generated in the FOV. Signals from the local coil arrangement 106 may be evaluated, for example, converted into images, stored, or displayed, by an evaluation device (e.g., including elements 168, 115, 117, 119, 120, 121) of the MRI scanner 101. The MRI scanner 101 may be connected via coaxial cables or radio (167), for example, to the local coil arrangement 106.

To examine the body 105 (e.g., the object to be examined or the patient) using the magnetic resonance imaging scanner 101 by magnetic resonance imaging, various magnetic fields are matched as accurately as possible in terms of temporal and spatial characteristics and are radiated onto the body 105. A strong magnet, (e.g., a cryomagnet 107) in a measuring cabin having a tunnel-shaped opening 103 produces a static strong main magnetic field $B_0$. The value of the main magnetic field $B_0$ may be, for example, 0.2 Tesla to 3 Tesla or more. The body 105 to be examined may be positioned on an examination table 104 and moved into a region of the main magnetic field $B_0$. Such a region may be roughly homogenous in the FOV. The nuclear spin of atomic nuclei in the body 105 is excited by magnetic high frequency excitation pulses radiated via a high frequency antenna and/or optionally a local coil arrangement. The local coil arrangement is shown in FIG. 7 in a simplified form as a multi-part body coil 108a, 108b, 108c. High frequency excitation pulses may be produced, for example, by a pulse-generating unit 109 controlled by a pulse sequence control unit 110. Following amplification by a high frequency amplifier 111, the high frequency excitation pulses may be conveyed to the high frequency antenna 108. The high frequency system illustrated here is merely schematically shown in FIG. 7. In other embodiments, more than one pulse-generating unit 109, more than one high frequency amplifier 111, and a plurality of high frequency antennae 108 a, b, c are used in a magnetic resonance imaging scanner 101.

The magnetic resonance imaging scanner 101 also includes gradient coils 112x, 112y, 112z. Magnetic gradient fields are radiated using the gradient coils 112x, 122y, 112z during a measurement for selective layer excitation and for spatial encoding of the measuring signal. The gradient coils 112x, 112y, 112z are controlled by a gradient coil control unit 114 that like the pulse-generating unit 109, is connected to the pulse sequence control unit 110.

Signals emitted by the excited nuclear spin of the atomic nuclei in the object being examined are received by the body coil 108 and/or at least one local coil arrangement 106. The signals are amplified by associated high frequency amplifiers 116, processed further and digitized by a receiving unit 117. The recorded measuring data are digitized and stored in a k-space matrix as complex numerical values. An associated MR image may be reconstructed from the k-space matrix occupied by values by a multi-dimensional Fourier transformation.

For a coil, which may be operated in both transmitting and receiving modes, such as the body coil 108 or a local coil 106, correct signal forwarding is regulated by a transceiver switch 118 connected upstream.

An image processing unit 119 produces an image from the measuring data. The image is displayed to a user via a control panel 120 and/or is stored in a memory unit 121. A central computer unit 122 controls the individual unit components.

In MR imaging, images with a high signal-to-noise ratio (SNR) are recorded using local coil arrangements (e.g., coils, local coils). Local coil arrangements may be antenna systems provided in the immediate vicinity above (anterior), below (posterior), on or in the body 105.

During an MR measurement, the excited cores induce a voltage in the individual antennae of the local coil. The induced voltage is amplified by a low-noise preamplifier (e.g., LNA or preamp) and is forwarded to the electronic receiving device. High-field units (e.g., 1.5 T-12 T or more) are used to improve the signal-to-noise ratio even in the case of high resolution images. To connect more individual antennae to an MR receiving system than there are receivers available, a switch matrix (e.g., an RCCS) may be fitted between receiving antennae and receivers. Such a switch matrix routes the instantaneously active receiving channels (e.g., the receiving channels located precisely in the FOV of the magnet) to the available receivers. Thus, more coil elements than there are receivers available may be connected in the case of whole body coverage since only the coils located in the field of view or the homogeneity volume of the magnet have to be read out.

An antenna system, which may include one antenna element or an array coil of a plurality of antenna elements (e.g., coil elements), may be designated a local coil arrangement 106. Individual antenna elements may be configured as loop antennae, butterfly antennae, flex coils, or saddle coils. A local coil arrangement may include coil elements, a preamplifier, further electronic devices (e.g., baluns), a housing, supports, and a cable, with which the local coil may be connected to the MRT unit. A receiver 168 may be provided on the unit that filters and digitizes a signal received from a local coil 106, for example, via radio, and passes the data to a digital signal processing device. Such a signal processing device derives an image or a spectrum from the data obtained by a measurement and makes the image available to the user for subsequent diagnosis by the user and/or storage.

FIGS. 1-6 show in a side view an exemplary local coil 106, with one or more local shim coils therein, positioned on the head and/or neck of a patient 106 at a region/a position PP.

Figure 1:
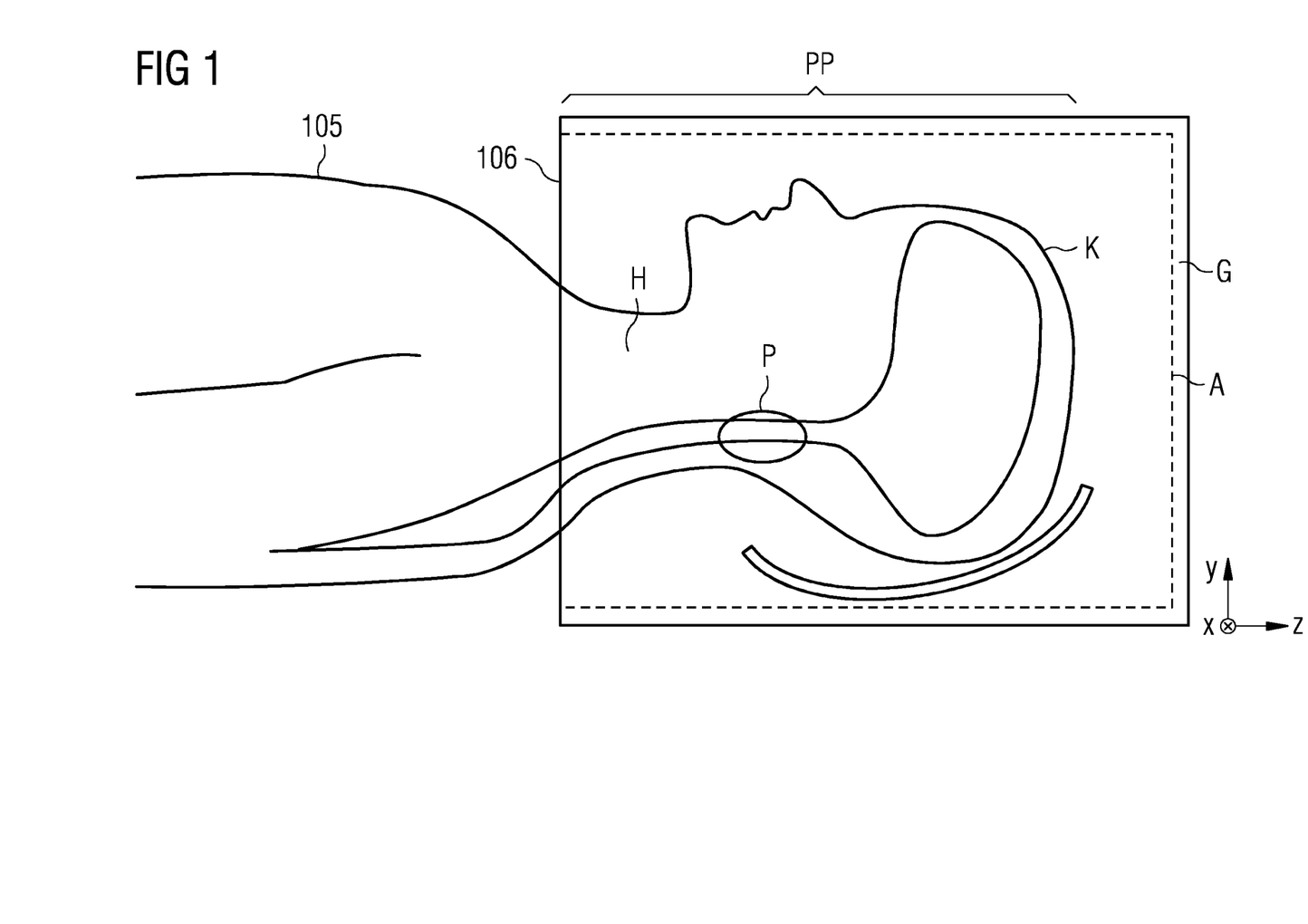
FIG. 1 shows a view from one side and in a longitudinal section of a patient and one embodiment of a head coil.

As FIG. 1 shows, a certain susceptibility jump may exist in a problem zone P in the transition region between the thorax and nape/head of a patient 105.

Such a susceptibility jump may be caused by spatially inhomogeneous field or susceptibility, distribution in the transition from thorax to the comparatively narrower neck-nape-head region, and/or due to air in the region of the patient's esophagus/windpipe.

The MRI scanner local coil 106 has an interior A (e.g., a cavity open only counter to the z direction, in the housing G or a region or space A surrounded only right+left+cranial+below or right+left+below by the housing G of the local coil). The head K, or the head K and neck H of a patient 105 may be positioned within the interior space A (e.g., position PP of the head K in the local coil 106 in FIG. 1). In the example of FIG. 1, the patient may put the local coil 106 on in the manner of a helmet, or the patient may lie on a lower part of the local coil, whereupon an upper part of the local coil may be folded over the patient's face.

Figure 2:
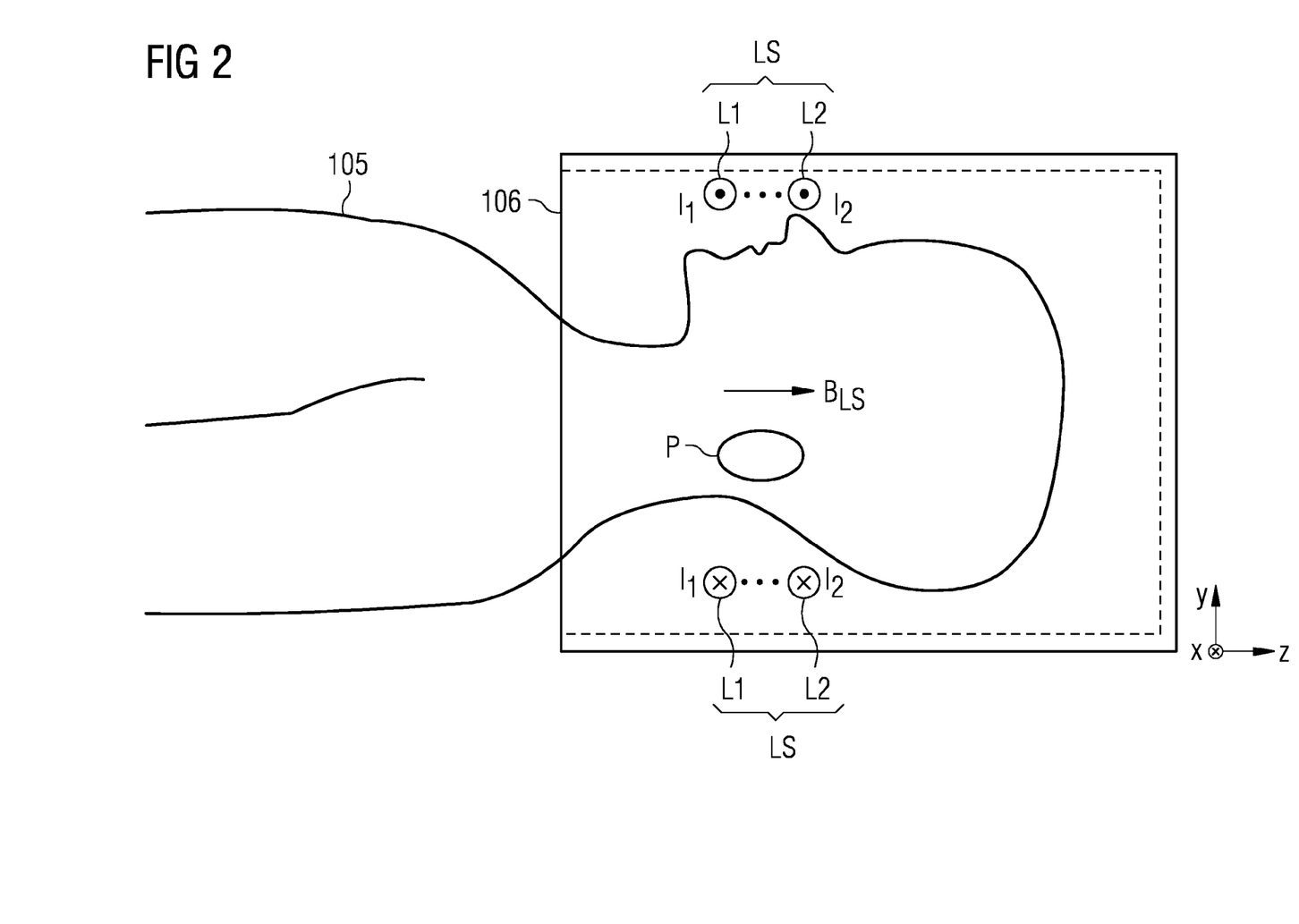
FIG. 2 shows a view from one side and in a longitudinal section of one embodiment of a shimmed local coil.

FIG. 2 shows one embodiment of integration of shim coil elements in a head-nape-local coil 106. The coil 106 is shown schematically simplified as a rectangle. The current directions (e.g., the directions, in which current I may flow in local shim coil elements LS in the local coil), and a field $B_{LS}$ produced by the local shim coil elements LS (e.g., a static $B_0'$ field) are shown in an exemplary and simplified manner.

In FIG. 2, a plurality of conductors L1, L2 (e.g., more than two conductors, of which two conductors L1, L2 are shown by way of example) of a local shim coil element LS in the local coil run approximately in the position of the nape region, and/or mouth region, and/or approximately/partially below (−y) a problem zone P of a patient. Such a patient may wear the local coil 105 like a helmet while lying. The local coil may extend around the head K, neck H of the patient, and/or the z axis in, for example, an approximately elliptical or oval or rectangular form.

In FIG. 2, current I1 flows in the conductor L1 in the illustrated sectional position above the head K out of the drawing plane counter to the x direction, as symbolized by a point in the conductor L1. In the illustrated sectional position below the head K, current I1 flows in the conductor L1 into the drawing plane in the x direction, as symbolized by a cross in the conductor L1. In the illustrated sectional position above the head K, current I2 flows in FIG. 2 in the conductor L2 out of the drawing plane counter to the x direction, as symbolized by a point in the conductor L2. In the illustrated sectional position below the head K, current I2 flows in the conductor L2 into the drawing plane in the x direction, as symbolized by a cross in the conductor L2.

The directional current flow in conductors L1 and L2 results in a magnetic field $B_{LS}$ produced by the local shim coil element LS in the local coil 105. The magnetic field $B_{LS}$ compensates, with respect to the $B_0$ field therein, the problem zone P to optimize images, which may be produced by the MRI scanner.

Viewed in the y direction, the conductors L1, L2 are at the same height (e.g., above an examination table) in FIG. 2.

Figure 3:
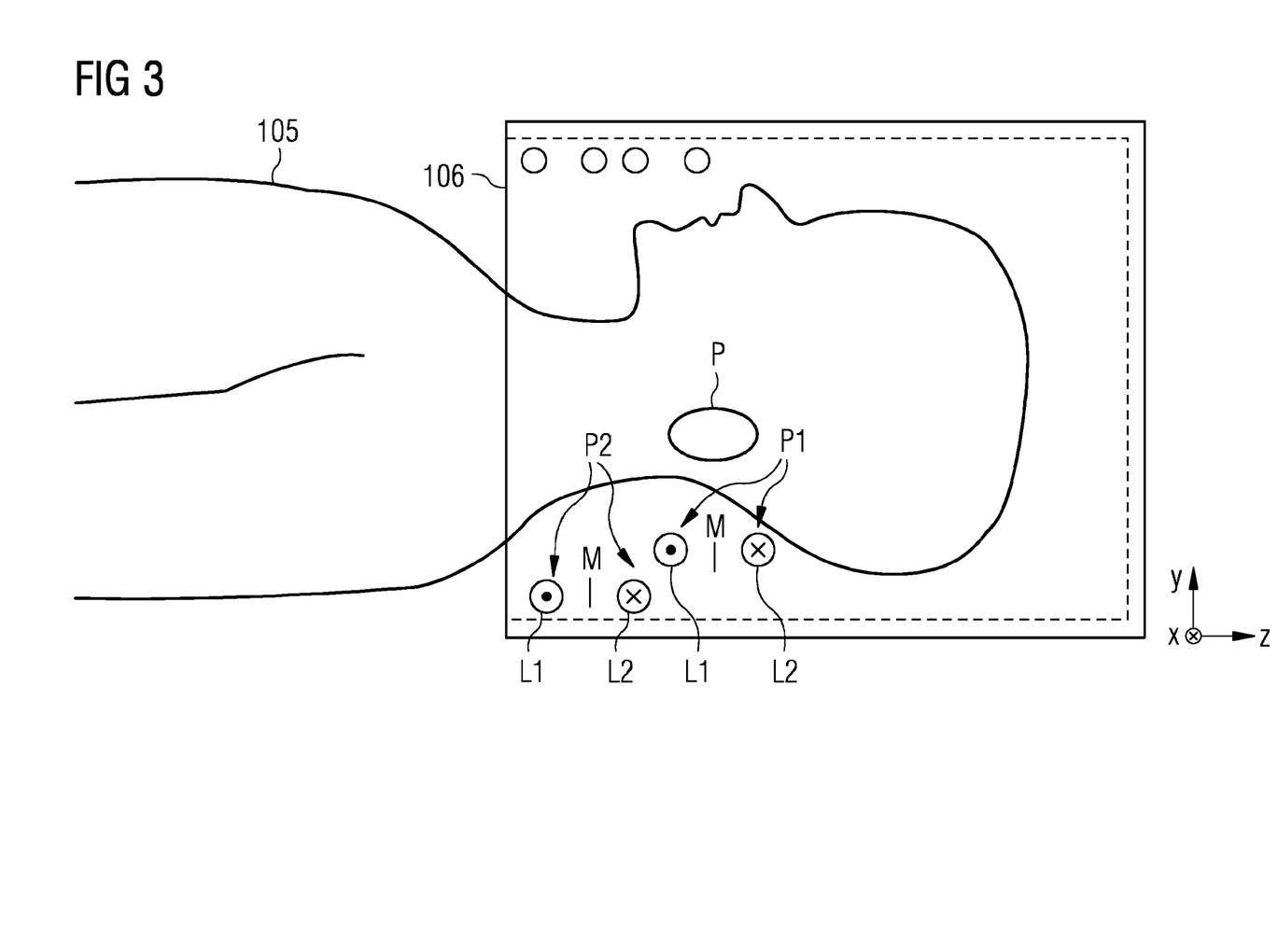
FIG. 3 shows a view from one side and in a longitudinal section of one embodiment of a shimmed local coil.

As another embodiment, FIG. 3 also shows integration of shim coil elements in a head-nape local coil 106. The coil 106 is shown schematically simplified as a rectangle.

Viewed in the y direction, the conductors L1, L2 are also at the same height as each other above an examination table in FIG. 3. In FIG. 3, conductors L1, L2 of a local shim coil element LS of the local coil 105 are shown arranged jointly in different positions relative to the problem zone P (e.g., the nape region of a patient) when viewed in the z direction. Depending on the position P1, P2, the different positions relative to the problem zone P cause a different magnetic field $B_{LS}$ produced by the local shim coil element LS of the local coil 105 (e.g., at a different position).

Depending on the spacing in the z direction of the shim coil center M (e.g., between the two conductors L1, L2 that are furthest apart from each other) from the problem zone P, stray fields of the shim coil are used differently to compensate for the $B_0$ inhomogeneity due to the problem zone P.

The conductors L1, L2 may be provided at a plurality of positions P1, P2 in a local coil 105. The conductors may be loaded with current only at one or some of the positions respectively to produce a magnetic field $B_{LS}$ in order to adjust the local coil to different patients.

Coils or conductors L1, L2 of the coils of a shim coil element LS may be located in the local coil 106 at a position P1, P2 anterior and/or posterior of a position PP for a patient. The position of the coils may be arranged on the head and/or neck of a patient and/or encompass a position PP for a patient.

Figure 4:
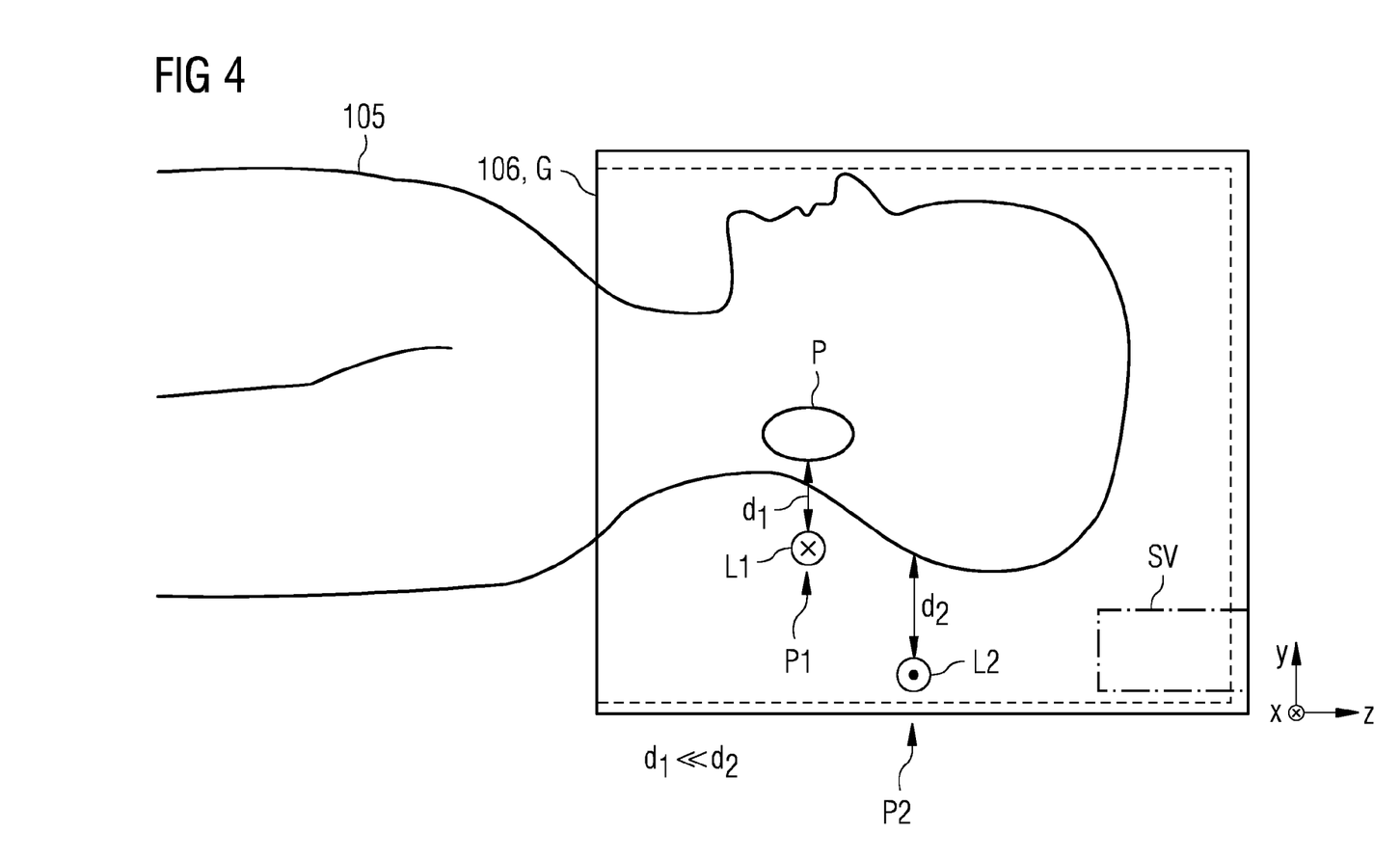
FIG. 4 shows a view from one side and in a longitudinal section of one embodiment of a shimmed local coil.

As one embodiment, FIG. 4 also shows integration of shim coil elements in a head-nape local coil 106. The coil 106 is shown schematically simplified as a rectangle.

Viewed in the y direction, the conductors L1, L2 are arranged at different heights d1, d2 relative to the problem zone P and/or above an examination table in the local coil (e.g., in the housing of the local coil) in FIG. 3.

The shim field of the conductor L1 or plurality of conductors, which conduct(s) the current in one direction directly next to the problem zone P, may be used for homogenization. The return takes place a relatively long distance from the problem zone, as shown here in the conductor L2.

Further possible embodiments may include the following examples. The shim current of the local coil 106 may be adapted by a current controller in the local coil and/or by a controller of the MRI scanner system 101, 117, 168.

The shim coil may be adapted in an iterative method including acts of estimating a shim current, adjusting the shim current, measuring homogeneity, estimating a new shim current, and repeating the acts.

A plurality of spatially distributed local shim coils in the local coil may be operated together or alternately by switching on and off and/or by the controller of the current, so the fields of the local shim coils overlap constructively or destructively. The local shim coils may be in the head, nape, and/or in a spine coil.

Local shim coils for extremity coils located a distance out in the X direction, such as a shoulder coil, may also be provided.

Figure 6:
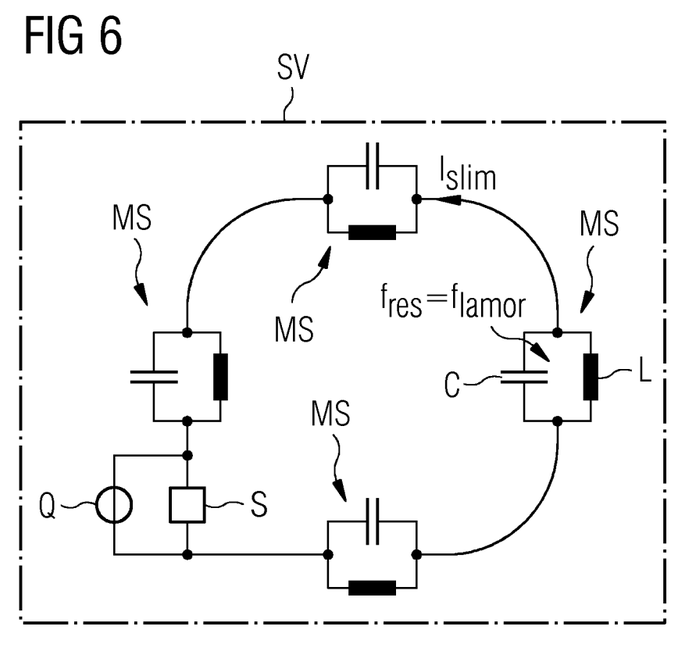
FIG. 6 shows a detailed view of a circuit diagram of a power supply of an exemplary local coil.

FIG. 6 shows a circuit diagram of an exemplary power supply SV of a local coil 106, indicated by a rectangle in broken lines.

Shim coils of the local coil are intended to suppress high currents in the HF transmitting frequency by baluns MS or parallel resonance filters (e.g., a coil and a capacitor).

In the illustrated example, current I flows across the low-resistance coils L.

The DC current source Q of the power supply SV may be controlled, for example. The DC source may be protected against an induction of high voltage fields by the gradient fields of the MRI scanner. A protective circuit S may be provided as a diode bridge.

A low-pass filter with very low frequency in the DC source power pack (f<ca 0 Hz) may be provided.

The shim coils, L1, L2, LS etc., may be securely mechanically connected to the local coil (106) housing G to be able to absorb the Lorentz forces of the gradient fields. Local shim coils may be integrated in the local coil and therefore compensate locally severely limited effects.

One possible advantage of an embodiment lies in integration of shim coil elements directly at the site of the local $B_0$ inhomogeneity within a local coil. Such integration allows the technical implementation of the shim coil, so the shim coil may be constructed to be resistant to high HF alternating fields and gradient fields and may be operated in a manner safe for the patient.

FIG. 4 shows an exemplary embodiment with a conductor L2 carrying current I2 in the "x" direction on the right. The conductor L2 is located approximately or exactly below the molded nape section (e.g., the nape region P2). The example of FIG. 4 also shows another conductor L1 carrying current I1 in the x direction. The conductor L1 is located approximately or exactly below the shoulder region (P1) (e.g., in the region of the C5/C6 vertebral bodies of a patient).

The coil arrangement shown in FIG. 4 is suitable if $B_0$ inhomogeneities are such that the field distortion in the nape region and in the shoulder region have opposing signs. These inhomogeneities may be compensated with at least one shim coil in that the feed conductors and return conductors (L1, L2) of the shim coils are used for precisely such compensating.

The conductors or conductor arrangements L1, L2 shown schematically in the figures may be a single conductor or a single wire in each case. The conductor arrangements L1, L2 may also potentially contain a plurality of conductors L1a, L1b, L1c, L1d or L2a, L2b, L2c, L2d that run side by side and parallel to each other.

Figure 5:
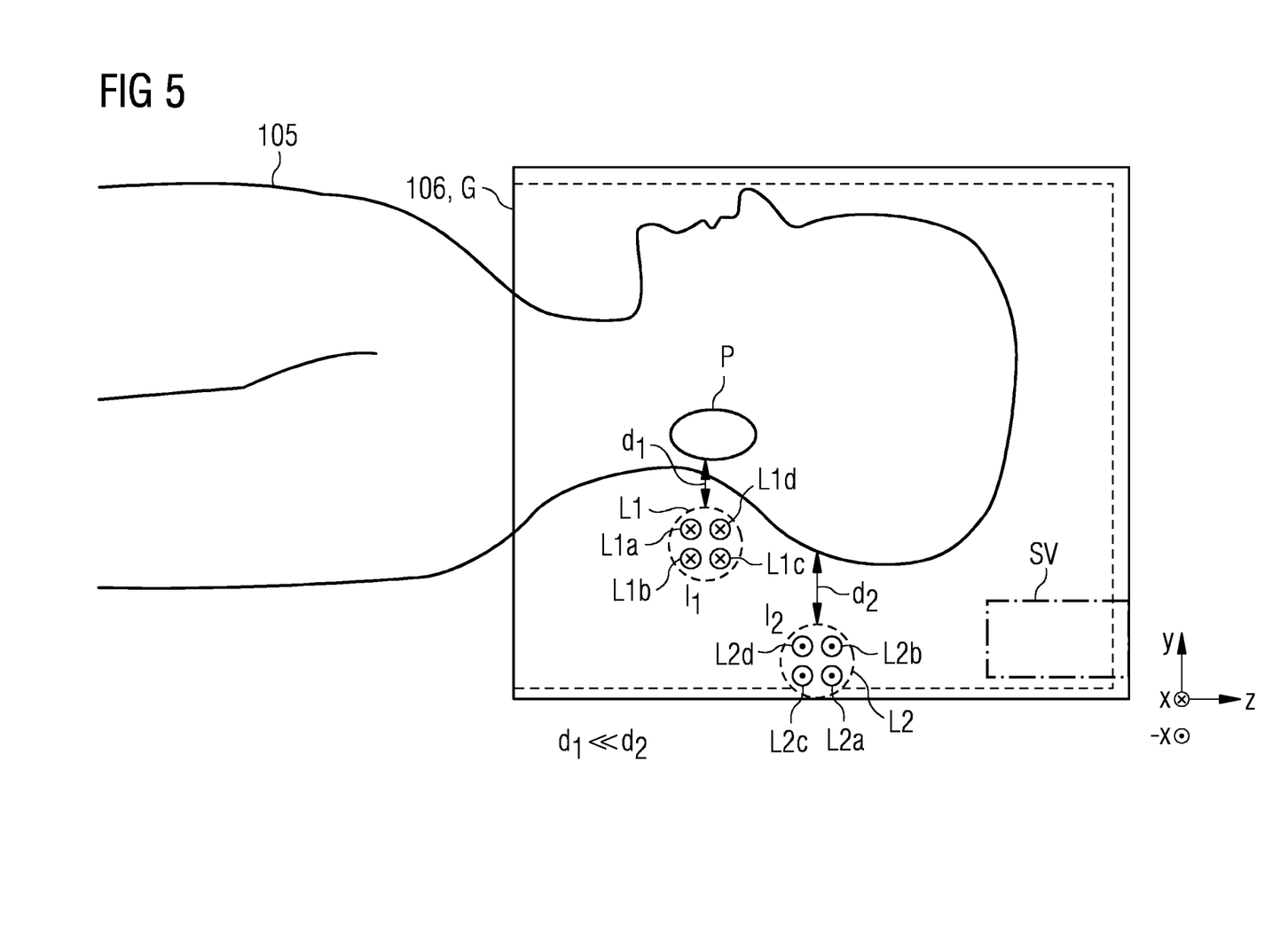
FIG. 5 shows a view from one side and in a longitudinal section of one embodiment of a shimmed local coil having local coil conductor assemblies with each local coil including a plurality of conductors.

FIG. 5 shows from one side in a longitudinal section a shimmed local coil having local coil conductor arrangements L1, L2 that each include a plurality of conductors or wires L1a, L1b, L1c, L1d or L2a, L2b, L2c, L2d.

The y spacing and possibly also the z spacing of the conductors L1 and L2 in FIG. 5 may be configured so as to be variable. The variable spacing may be achieved, for example, by electrically switching different conductor structures (e.g., simultaneously present in the local coil) or by different mechanical placement. The different spacings are advantageous for optimum adaptation to the susceptibility rates individual to the patient.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A local coil for an imaging system, the local coil comprising:
    a head coil comprising a housing, the housing including a first side, through which a patient extends when a head of a patient is positioned in the head coil, and a nape section shaped to support a nape of the patient, the nape section configured to extend from the first side to a plane parallel to the first side, the plane coinciding with a point on the back of the neck of the patient when the head of the patient is positioned in the head coil, the head coil configured so that the head of the patient is positionable in the head coil and the neck of the patient is positionable on the nape section of the housing; and
    at least one shim coil comprising a plurality of conductors, all conductors of the plurality of conductors being disposed in the nape section of the housing, all other regions of the head coil outside of the nape section not including any shim coils,
    wherein subsets of conductors of the plurality of conductors are loadable with current.

2. The local coil as claimed in claim 1, wherein the local coil is configured for use with a magnetic resonance imaging (MRI) scanner, and the head coil is an MRI scanner head coil.

3. The local coil as claimed in claim 2, wherein the at least one shim coil comprises a plurality of shim coils, and
    wherein the head coil, the MRI scanner, or the head coil and the MRI scanner comprise a controller of shim current in the plurality of shim coils.

4. The local coil as claimed in claim 3, wherein the plurality of shim coils are spatially distributed in the local coil and are operable together, are operable alternately to each other, or are operable together and alternately to each other, by switching on or off, via the controller of the shim current in the shim coils, or by switching on or off and via the controller of the shim current in the shim coils.

5. The local coil as claimed in claim 1, further comprising an inner space, wherein the head, the neck, or the head and the neck of the patient are positionable in the inner space.

6. The local coil as claimed in claim 1, wherein the head coil is placeable on the head, the neck, or the head and the neck of the patient.

7. The local coil as claimed in claim 1, wherein the head coil comprises one or more coils, the one or more coils being located in the local coil at a position anterior, a position posterior, or a position anterior and posterior of a position for the head, a position for the neck, or a position for the head and the neck, the one or more coils being located in the local coil encompassing a position for the head, a position for the neck, or a position for the head and the neck of the patient, or a combination thereof.

8. The local coil as claimed in claim 1, wherein the at least one shim coil is arranged in the housing of the local coil.

9. The local coil as claimed in claim 1, wherein a power supply, a controller, or a power supply and a controller of the at least one shim coil is arranged in a housing of the local coil.

10. The local coil as claimed in claim 1, wherein the at least one shim coil comprises exactly one shim coil.

11. The local coil as claimed in claim 1, wherein the at least one shim coil comprises two or more shim coils.

12. The local coil as claimed in claim 1, wherein the head coil is a head-neck local coil for head and neck combined.

13. The local coil as claimed in claim 1, wherein the at least one shim coil comprises a power supply, a current source of the power supply being controllable.

14. The local coil as claimed in claim 13, wherein the current source of the power supply comprises a protective circuit.

15. The local coil as claimed in claim 14, wherein the imaging system is a magnetic resonance imaging (MRI) scanner, and
    wherein the protective circuit is operable to protect against an induction of high voltage fields through gradient fields of the MRI scanner.

16. The local coil as claimed in claim 1, further comprising a power supply, the power supply comprising a diode bridge, a low-pass filter, or the diode bridge and the low pass filter, the low pass filter having a frequency in a DC source power pack of the power supply of less than 10 Hz.

17. The local coil as claimed in claim 1, wherein a shim coil of the at least one shim coil is configured to produce a constant magnetic field.

18. The local coil as claimed in claim 1, wherein the at least one shim coil comprises a plurality of shim coils, and
    wherein the plurality of shim coils is mechanically connected to the local coil housing.

19. The local coil as claimed in claim 1, wherein the at least one shim coil comprises a plurality of shim coils,
    wherein the shim coil is a first shim coil of the plurality of shim coils, and
    wherein a conductor of a second shim coil of the plurality of shim coils is arranged in a region for a shoulder region, a vertebral body, or the shoulder region and the vertebral body of the patient.

20. The local coil as claimed in claim 19, wherein the vertebral body comprises the C5 vertebrae or the C6 vertebrae.

21. The local coil as claimed in claim 1, wherein a shim coil of the at least one shim coil includes a first conductor and a second conductor at various positions, and
    wherein current flows in mutually opposed directions in the first conductor and the second conductor.

22. The local coil as claimed in claim 1, wherein a shim coil of the at least one shim coil includes a first conductor and a second conductor, and
    wherein, in at least a region of the local coil provided for positioning under the patient, current flows in mutually opposed directions in the first conductor and the second conductor.

23. The local coil as claimed in claim 1, wherein a shim coil of the at least one shim coil comprises a conductor, and
    wherein the conductor is a conductor arrangement including a plurality of lines that run, are located, or run and are located side by side.

24. The local coil as claimed in claim 1, wherein a shim coil of the at least one shim coil comprises two or more assemblies of conductors, and
    wherein a y spacing of first conductors of the two or more assemblies of conductors from each other is greater or smaller than a y spacing of second conductors of the two or more assemblies of conductors from each other, a z spacing of the first conductors of the two or more assemblies of conductors from each other is greater or smaller than a z spacing of the second conductors of the two or more assemblies of conductors from each other, or the y spacing of the first conductors of the two or more assemblies of conductors from each other is greater or smaller than the y spacing of the second conductors of the two or more assemblies of conductors from each other and the z spacing of the first conductors of the two or more assemblies of conductors from each other is greater or smaller than the z spacing of the second conductors of the two or more assemblies of conductors from each other.

25. The local coil as claimed in claim 1, further comprising a switching device operable to electrically switch on various conductor structures in the local coil, wherein the switching device is operable to switch on only first conductors of the various conductor structures for shimming, only second conductors of the various conductor structures for shimming, or the first conductors and the second conductors for shimming.

* * * * *